United States Patent [19]

Mayer

[11] Patent Number: 5,800,511
[45] Date of Patent: Sep. 1, 1998

[54] CLAD COMPOSITE STENT

[75] Inventor: David W. Mayer, Bloomington, Minn.

[73] Assignee: Schneider (USA) Inc., Plymouth, Minn.

[21] Appl. No.: 485,626

[22] Filed: Jun. 7, 1995

Related U.S. Application Data

[62] Division of Ser. No. 6,216, Jan. 19, 1993, abandoned.

[51] Int. Cl.⁶ .................................................. A61F 2/06
[52] U.S. Cl. .................................................. 623/1
[58] Field of Search .................................. 623/1, 11, 12;
606/191, 192, 194, 195, 198

[56] References Cited

U.S. PATENT DOCUMENTS

| | | | |
|---|---|---|---|
| 2,524,661 | 10/1950 | Harder et al. | |
| 3,466,166 | 9/1969 | Levinstein et al. | |
| 3,562,024 | 2/1971 | Smith et al. | |
| 4,023,557 | 5/1977 | Thorne et al. | |
| 4,281,419 | 8/1981 | Treace | 3/1.9 |
| 4,465,481 | 8/1984 | Blake | |
| 4,600,446 | 7/1986 | Torisaka et al. | |
| 4,655,771 | 4/1987 | Wallsten | 623/1 |
| 4,719,916 | 1/1988 | Ravo | |

(List continued on next page.)

FOREIGN PATENT DOCUMENTS

| | | |
|---|---|---|
| 547 739 A1 | 6/1993 | European Pat. Off. |
| 556 940 A1 | 8/1993 | European Pat. Off. |
| 593 136 A1 | 4/1994 | European Pat. Off. |
| 067 929 | 12/1982 | Germany |
| 0259541 | 10/1989 | Japan |

OTHER PUBLICATIONS

Search Report in PCT/US93/11262 Info. Sheet "Drawn Filled Tubing" Published by Fort Wayne Metal Research Projects.
WO 93/19803 "Medical Wire"; Oct. 1993; Heath et al.
WO 93/19804 "Tubular Medical Endoprostheses"; Oct. 1993; Heath et al.
WO 92/13483 "Multifilar Coil Guide Wire"; Aug. 1992; Fleischhacker, et al.
WO 94/16646 "Clad Composite Stent"; Aug. 1994; Mayer.
PCT/US93/11262, Search Report; Nov. 1993; Schneider (USA) Inc "DFT—Drawn Filled Tubing".
"Intravascular Stents to Prevent Occlusion and Restenosis After Transluminal Angioplasty", The New England Journal of Medicine, Sigwart et al., vol. 316, Mar. 19, 1987, No. 12.
"Strengthening mechanisms in Elgiloy", Journal of Materials Science, Assefpour–Dezfuly et al; Nov. 1983; pp. 2815–2836.
PCT/IB 95/00253, Search Report, Oct. 1995, Schneider (USA) Inc.
1991 Annual Book of ASTM Standards, vol. 13.01 Medical Devices.

Primary Examiner—John G. Weiss
Assistant Examiner—John M. Black
Attorney, Agent, or Firm—Haugen and Nikolai, P.A.

[57] ABSTRACT

A body compatible stent is formed of multiple filaments arranged in two sets of oppositely directed helical windings interwoven with one another in a braided configuration. Each of the filaments is a composite including a central core and a case surrounding the core. In the more preferred version, the core is formed of a radiopaque and relatively ductile material, e.g. tantalum or platinum. The outer case is formed of a relatively resilient material, e.g. a cobalt/chromium based alloy. Favorable mechanical characteristics of the stent are determined by the case, while the core enables in vivo imaging of the stent. The composite filaments are formed by a drawn filled tubing process in which the core is inserted into a tubular case of a diameter substantially more than the intended final filament diameter. The composite filament is cold-worked in several steps to reduce its diameter, and annealed between successive cold-working steps. After the final cold working step, the composite filament is formed into the desired shape and age hardened. Alternative composite filaments employ an intermediate barrier layer between the case and core, a biocompatible cover layer surrounding the case, and a radiopaque case surrounding a structural core.

41 Claims, 2 Drawing Sheets

U.S. PATENT DOCUMENTS

| | | |
|---|---|---|
| 4,731,084 | 3/1988 | Dunn et al. . |
| 4,830,262 | 5/1989 | Ishibe . |
| 4,848,348 | 7/1989 | Craighead . |
| 4,883,486 | 11/1989 | Kapadia et al. . |
| 4,950,227 | 8/1990 | Savin et al. . |
| 5,001,825 | 3/1991 | Halpern . |
| 5,003,987 | 4/1991 | Grinwald . |
| 5,003,989 | 4/1991 | Taylor et al. . |
| 5,015,253 | 5/1991 | MacGregor . |
| 5,024,232 | 6/1991 | Smid et al. . |
| 5,047,050 | 9/1991 | Arpesani . |
| 5,059,166 | 10/1991 | Fischell et al. ............................ 600/3 |
| 5,069,226 | 12/1991 | Yamauchi et al. . |
| 5,092,877 | 3/1992 | Pinchuk . |
| 5,104,404 | 4/1992 | Wolff . |
| 5,139,480 | 8/1992 | Hickle et al. . |
| 5,201,901 | 4/1993 | Harada et al. . |
| 5,207,706 | 5/1993 | Menaker . |
| 5,213,111 | 5/1993 | Cook et al. ............................ 128/772 |
| 5,217,483 | 6/1993 | Tower . |
| 5,256,764 | 10/1993 | Tang et al. . |
| 5,320,100 | 6/1994 | Herweck et al. . |
| 5,360,442 | 11/1994 | Dahl et al. . |
| 5,374,261 | 12/1994 | Yoon . |
| 5,382,259 | 1/1995 | Phelps et al. . |
| 5,389,106 | 2/1995 | Tower . |
| 5,514,154 | 5/1996 | Lau et al. . |

CLAD COMPOSITE STENT

This application is a division of U.S. application Ser. No. 08/006,216 filed 19 Jan. 1993, now abandoned.

BACKGROUND OF THE INVENTION

The present invention relates to body implantable medical devices, and more particularly to stents and other prostheses configured for high radio-opacity as well as favorable mechanical characteristics.

Recently several prostheses, typically of lattice work or open frame construction, have been developed for a variety of medical applications, e.g. intravascular stents for treating stenosis, prostheses for maintaining openings in the urinary tracts, biliary prostheses, esophageal stents, renal stents, and vena cava filters to counter thrombosis. One particularly well accepted device is a self-expanding mesh stent disclosed in U.S. Pat. No. 4,655,771 (Wallsten). The stent is a flexible tubular braided structure formed of helically wound thread elements. The thread elements can be constructed of a biocompatible plastic or metal, e.g. certain stainless steels, polypropylene, polyesters and polyurethanes.

Alternatively, stents and other prostheses can be expandable by plastic deformation, usually by expanding a dilation balloon surrounded by the prosthesis. For example, U.S. Pat. No. 4,733,665 (Palmaz) discloses an intraluminal graft constructed of stainless steel strands, either woven or welded at their intersections with silver. U.S. Pat. No. 4,886,062 (Wiktor) features a balloon expandable stent constructed of stainless steel, a copper alloy, titanium, or gold.

Regardless of whether the prosthesis is self-expanding or plastically expanded, accurate placement of the prosthesis is critical to its effective performance. Accordingly, there is a need to visually perceive the prosthesis as it is being placed within a blood vessel or other body cavity. Further, it is advantageous and sometimes necessary to visually locate and inspect a previously deployed prosthesis.

Fluoroscopy is the prevailing technique for such visualization, and it requires radio-opacity in the materials to be imaged. The preferred structural materials for prosthesis construction, e.g. stainless steels and cobalt-based alloys, are not highly radiopaque. Consequently, prostheses constructed of these materials do not lend themselves well to fluoroscopic imaging.

Several techniques have been proposed, in apparent recognition of this difficulty. For example, U.S. Pat. No. 4,681,110 (Wiktor) discloses a self-expanding blood vessel liner formed of woven plastic strands, radially compressed for delivery within a tube. A metal ring around the tube is radiopaque. Similarly, U.S. Pat. No. 4,830,003 (Wolff) discusses confining a radially self-expanding stent within a delivery tube, and providing radiopaque markers on the delivery tube. This approach facilitates imaging only during deployment and initial placement.

To permit fluoroscopic imaging after placement, the stent itself must be radiopaque. The Wolff patent suggests that the stent can be formed of platinum or a platinum-iridium alloy for substantially greater radio-opacity. Such stent, however, lacks the required elasticity, and would exhibit poor resistance to fatigue. The Wiktor '110 patent teaches the attachment of metal staples to its blood vessel liner, to enhance radio-opacity. However, for many applications (e.g. in blood vessels), the stent is so small that such staples either would be too small to provide useful fluoroscopic imaging, or would adversely affect the efficiency and safety of deploying the stent or other prosthesis. This Wiktor patent also suggests infusing its plastic strands with a suitable fillers e.g. gold or barium sulfate, to enhance radio-opacity. Wiktor provides no teaching as to how this might be done. Further, given the small size of prostheses intended for blood vessel placement, this technique is unlikely to materially enhance radio-opacity, due to an insufficient amount and density of the gold or barium sulfate.

Therefore, it is an object of the present invention to provide a stent or other prosthesis with substantially enhanced radio-opacity, without any substantial reduction in the favorable mechanical properties of the prosthesis.

Another object is to provide a resilient body insertable composite filament having a high degree of radio-opacity and favorable structural characteristics, even for stents employing relatively small diameter filaments.

A further object is to provide a process for manufacturing a composite filament consisting essentially of a structural material for imparting desired mechanical characteristics, in combination with a radiopaque material to substantially enhance fluoroscopic imaging of the filament.

Yet another object is to provide a case composite prosthesis in which a highly radiopaque material and a structural material cooperate to provide mechanical stability and enhanced fluoroscopic imaging, and further are selectively matched for compatibility as to their crystalline structure, coefficients of thermal expansion, and annealing temperatures.

SUMMARY OF THE INVENTION

To achieve these and other objects, there is provided a process for manufacturing a resilient body insertable composite filament. The process includes the following steps:

a. providing an elongate cylindrical core substantially uniform in lateral cross-section and having a core diameter, and an elongate tubular case or shell substantially uniform in lateral cross-section and having a case inside diameter, wherein one of the core and case is formed of a radiopaque material and the other is formed of a resilient material having an yield strength (0.2% offset) of at least 150,000 psi, wherein the core diameter is less than the interior diameter of the case, and the lateral cross-sectional area of the core and case is at most ten times the lateral cross-sectional area of the core;

b. inserting the core into the case to form an elongate composite filament in which the case surrounds the core;

c. cold-working the composite filament to reduce the lateral cross-sectional area of the composite filament by at least 15%, whereby the composite filament has a selected diameter less than an initial outside diameter of composite filament before cold-working;

d. annealing the composite filament after cold-working, to substantially remove strain hardening and other stresses induced by the cold-working step;

e. mechanically forming the annealed composite filament into a predetermined shape; and f. after the cold-working and annealing steps, and while maintaining the composite filament in the predetermined shape, age hardening the composite filament.

In one preferred version of the process, the radiopaque material has a linear attenuation coefficient, at 100 KeV, of at least 25 $cm^{-1}$. The radiopaque material forms the core, and is at least as ductile as the case. The outside diameter of the composite filament, before cold-working, preferably is at most about six millimeters (about 0.25 inches). The cold-working step can include drawing the composite filament serially through several dies, with each die plastically deforming the composite filament to reduce the outside diameter. Whenever a stage including one or more cold-working dies has reduced the cross-sectional area by at least 25%, an annealing step should be performed before any further cold-working.

During each annealing step, the composite filament is heated to a temperature in the range of about 1900°–2300° F. for a period depending on the filament diameter, typically in the range of several seconds to several minutes. The core material and cladding (case) materials preferably are selected to have overlapping annealing temperature ranges, and similar coefficients of thermal expansion. The core and case materials further can be selectively matched as to their crystalline structure and metallurgical compatibility.

In an alternative version of the process, the initial outside diameter of the composite structure (billet) typically is at least fifty millimeters (about two inches) in diameter. Then, before cold-working, the composite filament is subjected to temperatures in the annealing range while the outside diameter is substantially reduced, either by swaging or by pulltrusion, in successive increments until the outside diameter is at most about 6 millimeters (0.25 inches). The resulting filament is processed as before, in alternative cold-working and annealing stages.

Further according to the process, the composite filament can be severed into a plurality of strands. Then, the strands are arranged in two oppositely directed sets of parallel helical windings about a cylindrical form, with the strands intertwined in a braided configuration to form multiple intersections. Then, while the strands are maintained in a predetermined uniform tension, they are heated to a temperature in the range of about 700°–1200° F., more preferably 900°–1000° F., for a time sufficient to age harden the helical windings.

The result of this process is a resilient, body implantable prosthesis. The prosthesis has a plurality of resilient strands, helically wound in two oppositely directed sets of spaced apart and parallel strands, interwoven with one another in a braided configuration. Each of the strands includes an elongate core and an elongate tubular case surrounding the core. A cross-sectional area of the core is at least ten percent of the cross-sectional area of the strand. The core is constructed of a first material having a linear attenuation coefficient of at least 25 cm$^{-1}$ at 100 KeV. The case is constructed of a resilient second material, less ductile than the first material.

More generally, the process can be employed to form a body compatible device comprising an elongate filament substantially uniform in lateral cross-section over its length and including an elongate cylindrical core and an elongate tubular case surrounding the core. One of the core and case is constructed of a first material having an yield strength (0.2% offset) of at least twice that of the second material. The other of the core and case is constructed of a second material being radiopaque and at least as ductile as the first material.

In a highly preferred version of the invention, the core is constructed of tantalum for radio-opacity, and the case is constructed of a cobalt-based alloy, e.g. as available under the brand names "Elgiloy", "Phynox" and "MP35N". The "Elgiloy" and "Phynox" alloys contain cobalt, chromium, nickel, and molybdenum, along with iron. Either of these alloys is well matched with tantalum, in terms of overlapping annealing temperature ranges, coefficients of thermal expansion and crystalline structure. The tantalum core and alloy case can be contiguous with one another, with virtually no formation of intermetallics.

When otherwise compatible core and case materials present the risk of intermetallic formation, an intermediate layer, e.g. of tantalum, niobium, or platinum, can be formed between the core and the case to provide a barrier against intermetallic formation. Further, if the case itself is not sufficiently biocompatible, a biocompatible coating or film can surround the case. Tantalum, platinum, iridium and their alloys, or stainless steels can be used for this purpose.

While disclosed herein in connection with a radially self-expanding stent, the composite filaments can be employed in constructing other implantable medical devices, e.g. vena cava filters, blood filters and thrombosis coils. Thus, in accordance with the present invention there is provided a resilient, body compatible prosthesis which, despite being sufficiently small for placement within blood vessels and similarly sized body cavities, has sufficient radio-opacity for fluoroscopic imaging based on the prosthesis materials themselves.

IN THE DRAWINGS

For a further understanding of the above and other features and advantages, reference is made to the following detailed description and to the drawings, in which.

DETAILED DESCRIPTION OF THE PREFERRED EMBODIMENT

Figure 1:
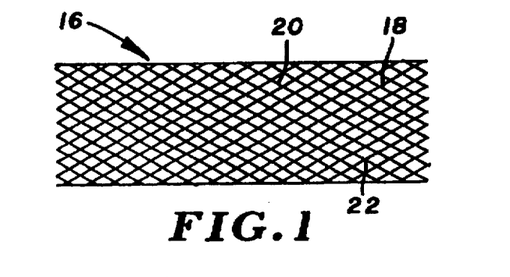
FIG. 1 is a side elevation of a self-expanding stent constructed according to the present invention.
Figure 2:
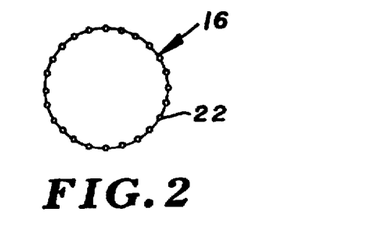
FIG. 2 is an end elevational view of the stent.

Turning now to the drawings, there is shown in FIGS. 1 and 2 a body implantable prosthesis 16, frequently referred to as a stent. Stent 16 is of open mesh or weave construction, consisting of two sets of oppositely directed, parallel and spaced apart helically wound strands or filaments indicated at 18 and 20, respectively. The sets of strands are interwoven in an over and under braided configuration to form multiple intersections, one of which is indicated at 22.

Stent 16 is illustrated in its relaxed state, i.e. in the configuration it assumes when subject to no external stresses. The filaments or strands of stent 16 are resilient, permitting a radial compression of the stent into a reduced-radius, extended-length configuration suitable for transluminal delivery of the stent to the intended placement site. As a typical example, stent 16 can have a diameter of about ten millimeters in the relaxed state, and is elastically compressed to a diameter of about 2 millimeters (0.08 inches) and an axial length of about twice the axial length of the relaxed stent. However, different applications call for different diameters. Further, it is well known to predetermine the degree of axial elongation for a given radial compression, by selectively controlling the angle between the oppositely directed helical strands.

Inelastic open-weave prostheses, expandable for example by dilation balloons, provide an alternative to resilient prostheses. Resilient or self-expanding prostheses often are preferred, as they can be deployed without dilation balloons or other stent expanding means. Self-expanding stents can be preselected according to the diameter of the blood vessel or other intended fixation site. While their deployment requires skill in stent positioning, such deployment does not require the additional skill of carefully dilating the balloon to plastically expand the prosthesis to the appropriate diameter. Further, the self-expanding stent remains at least slightly elastically compressed after fixation, and thus has a restoring force which facilitates acute fixation. By contrast, a plastically expanded stent must rely on the restoring force of deformed tissue, or on hooks, barbs, or other independent fixation elements.

Accordingly, materials forming the strands for filaments must be strong and resilient, biocompatible, and resistant to fatigue and corrosion. Vascular applications require hemocompatibility as well. Several materials meet these needs, including stainless "spring" steels, and certain cobalt-based alloys: more particularly two alloys including cobalt, chromium, iron, nickel and molybdenum sold under the brand names "Elgiloy" (available from Carpenter Technology Corporation of Reading, Pennsylvania) and "Phynox" (available from Metal Imphy of Imphy, France), respectively. Another suitable cobalt-chromium alloy is available under the brand name "MP35N" from Carpenter Technology Corporation of Reading, Pa.

Further, it is advantageous to form a prosthesis with substantial open space to promote embedding of the stent into tissue, and fibrotic growth through the stent wall to enhance long-term fixation. A more open construction also enables substantial radial compression of the prosthesis for deployment. In a typical construction suitable for transluminal implantation, the filaments can have a diameter of about 0.1 millimeter (0.004 inches), with adjacent parallel filaments spaced apart from one another by about 1–2 millimeters (0.04–0.08 inches) when the stent is in the relaxed state.

Fluoroscopic imaging of a conventional open weave prosthesis is extremely difficult. Due to their minute diameters and the materials involved, the filaments exhibit a relatively poor contrast to-body tissue for fluoroscopic imaging purposes. The filaments also require a high degree of spatial resolution in the imaging equipment involved. Thus, a stent recognizable on X-ray film may not be distinguishable for real time imaging, due to the relatively poor spatial resolution of the video monitor as compared to X-ray film.

Figure 3:
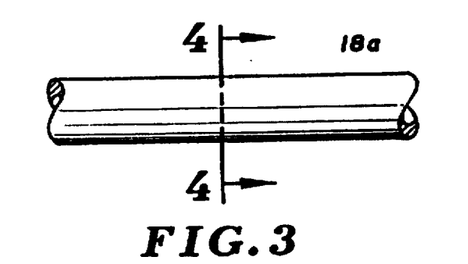
FIG. 3 is an enlarged partial view of one of the composite filaments forming the stent.
Figure 4:
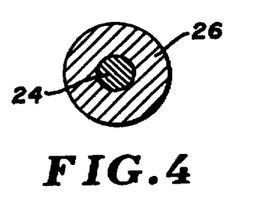
FIG. 4 is an enlarged sectional view taken along the line 4—4 in FIG. 3.

According to the present invention, however, prosthesis 16 is substantially more amenable to fluoroscopic imaging, due to the construction of strands 18 and 20. In particular, the strands cooperate to present a sufficiently radiopaque mass at the tangents of device 16 (parallel to the X-rays) for satisfactory real time imaging. As seen in FIGS. 3 and 4, a filament 18a of the prosthesis is of composite construction, with a radiopaque core 24 surrounded by and concentric with an annular resilient case 26. Core 24 is highly absorptive of X-rays, preferably having a linear attenuation coefficient of at least 25 (and more preferably at least 50) cm$^{-1}$ at 100 KeV. Materials with relatively high atomic numbers and densities tend to have the necessary attenuation coefficients. More particularly, it has been found that materials with an atomic number (elements) or "effective" atomic number (based on a weighted average of elements in alloys or compounds) of at least fifty, and densities of at least 0.5 pounds per cubic inch, exhibit the required ability to absorb X-rays. Finally, core 24 is preferably a ductile material so that it readily conforms to the shape of the case.

By contrast, case 26 is formed of a highly resilient material, preferably with a yield strength (0.2% offset) of at least 150,000 psi. More preferably, the yield strength is at least 300,000 psi. Consequently, the mechanical behavior of composite filament 18a in terms of elastic deformation in response to external stresses is, essentially, the behavior of case 26.

In addition to individual characteristics of the core and case, it is desirable to selectively match core and case materials based on certain common characteristics. The core and case materials should have the same or substantially the same linear coefficients of thermal expansion. Similarity of core and case materials in their crystalline structure is also an advantage. Finally, the core and case materials should have an overlap in their annealing temperature ranges, to facilitate manufacture of the filaments according to the process to be explained.

In a highly preferred embodiment, core 24 is formed of tantalum, and case 26 is formed of a cobalt-based alloy, more particularly Elgiloy (brand) alloy. Tantalum is a ductile metal having an atomic number of 73 and a density of about 0.6 pounds per cubic inch. Its linear attenuation coefficient, at 100 KeV, is 69.7 cm$^{-1}$.

The Elgiloy alloy includes principally cobalt and chromium, and has an effective atomic number of less than thirty and a density substantially less than 0.5 pounds per cubic inch. However, the alloy is body compatible, hemocompatible and highly resilient, with a yield strength (0.2% offset) of at least 350,000 psi, after cold working and age hardening.

Case 26 and core 24 thus cooperate to provide a prosthesis that can be viewed in vivo, and in real time. Of course, the amount of core material in relation to the amount of case material must be sufficient to insure radio-opacity while maintaining the favorable mechanical characteristics of stent 16. It has been found that the area of core 24, taken along a transverse or lateral plane as illustrated in FIG. 4, should be within the range of about ten percent to forty-six percent of the filament lateral cross-sectional area, i.e. the area of the combined case and core.

Tantalum and the Elgiloy alloy are well matched, in that the materials have similar linear coefficients of thermal expansion (3.6×10$^{-6}$ per degree F. and 8.4×10$^{-6}$ per degree F., respectively), similar crystalline structures, and annealing temperatures in the range of 1900°–2300° F. Further, there is virtually no tendency for the formation of intermetallic compounds along the tantalum/Elgiloy alloy interface.

Platinum and platinum alloys (e.g. platinum iridium) also are suitable as materials for core 24. The atomic number of platinum is 78, and its density is 0.775 pounds per cubic inch. Its linear attenuation coefficient at 100 KeV is 105 cm$^{-1}$. The linear coefficient of thermal expansion for platinum is about 4.9 ×10$^{-6}$ per degree F.

Thus, as compared to tantalum, platinum is structurally more compatible with the Elgiloy alloy, and more effectively absorbs X-rays. Accordingly, platinum is particularly well suited for use in prostheses formed of small diameter filaments. The primary disadvantage of platinum, with respect to tantalum, is its higher cost.

Further materials suitable for radiopaque core 24 include gold, tungsten, iridium, rhenium, ruthenium, and depleted uranium.

Other materials suitable for case 26 include other cobalt-based alloys, e.g. the Phynox and MP35N brand alloys. Cobalt-chromium and cobalt-chromium-molybdenum orthopedic type alloys also can be employed, as well as alloys of titanium-aluminum-vanadium. The MP35N alloy is widely available, and has a potential for better fatigue strength due to improved manufacturing techniques, particularly as to the vacuum melting process. The titanium-aluminum-vanadium alloys are highly biocompatible, and have more moderate stress/strain responses, i.e. lower elastic moduli.

Figure 7:
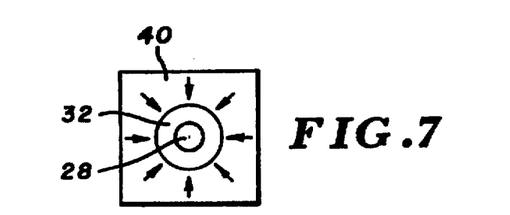
Figure 8:
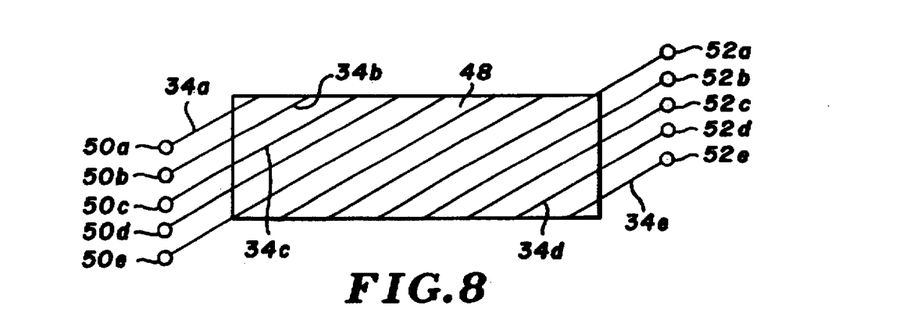
Figure 9:
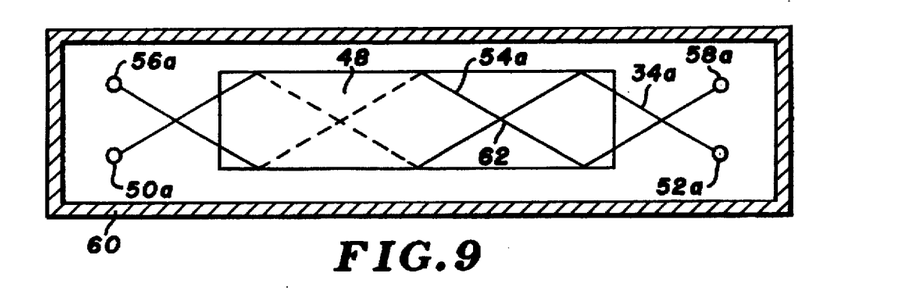

Composite filaments such as filament 18a are manufactured by a drawn filled tubing (DFT) process illustrated schematically in FIGS. 7-9. The DFT process can be performed, for example, by Fort Wayne Metals Research Products Corporation of Ft. Wayne, Ind. The process begins with insertion of a solid cylinder or wire 28 of the core material into a central opening 30 of a tube 32 of the case material. Core wire 28 and tubing 32 are substantially uniform in transverse or lateral sections, i.e. sections taken perpendicular to the longitudinal or axial dimension. For example, tube 32 can have an outer diameter d1 of about 0.102 inch (2.6 mm) and an inner diameter d2 (diameter of opening 30) of about 0.056 inches (1.42 mm). Core or wire 28 has an outer diameter d3 slightly less than the tube inner diameter, e.g. 0.046 inches (1.17 mm). In general, the wire outer diameter is sufficiently close to the tubing inner diameter to insure that core or wire 28, upon being inserted into opening 30, is substantially radially centered within the tubing. At the same time, the interior tubing diameter must exceed the core outside diameter sufficiently to facilitate insertion of the wire into an extended length of wire and tubing, e.g. at least twenty feet.

The values of the tubing inner diameter and the core outer diameter vary with the materials involved. For example, platinum as compared to tantalum has a smoother exterior finish when formed into the elongate wire or core. As a result, the outer diameter of a platinum wire can more closely approximate the inner diameter of the tube. Thus it is to be appreciated that the optimum diameter values vary with the materials involved, and the expected length of the composite filament.

Figure 6:
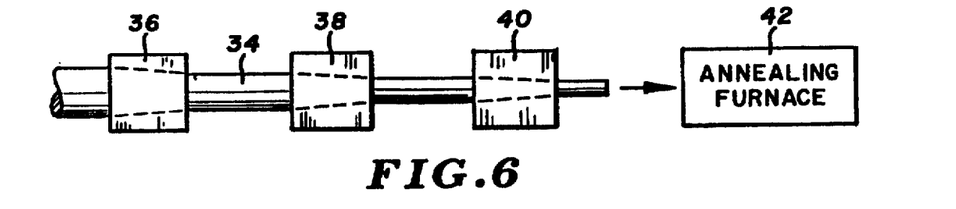

In any event, insertion of the core into the tube forms a composite filament 34, which then is directed through a series of alternating cold-working and annealing steps, as indicated schematically in FIG. 6. More particularly, composite filament 34 is drawn through three dies, indicated at 36, 38, and 40, respectively. In each of the dies, composite filament 34 is cold-worked in radial compression, causing the case tube 32 and the tantalum core wire 28 to cold flow in a manner that elongates the filament while reducing its diameter. Initially, case tube 32 is elongated and radially reduced to a greater extent than core wire 28, due to the minute radial gap that allowed the insertion of the core into the tube. However, the radial gap is closed rapidly as the filament is drawn through die 36, with subsequent pressure within die 36 and the remaining dies cold-working both the core and case together as if they were a single, solid filament. In fact, upon closure of the radial gap, the cold-working within all dies forms a pressure weld along the entire interface of the core and case, to form a bond between the core and case material.

As composite filament 34 is drawn through each die, the cold-working induces strain hardening and other stresses within the filament. Accordingly, one or more heating stages are provided, e.g. furnace 42. At each annealing stage, composite filament 34 is heated to a temperature in the range of from about 1900° to about 2300° F., or more preferably 2000°-2150° F. At each annealing stage, substantially all of the induced stresses are removed from the case and core, to permit further cold-working. Each annealing step is accomplished in a brief time, e.g. in as few as one to fifteen seconds at annealing temperature, depending on the size of composite filament 34.

While FIG. 6 illustrates one cold-working stage and annealing stage, it is to be understood that the appropriate number of stages is selected in accordance with the desired final filament size, the desired degree of cross-sectional area reduction during the final cold-working stage, and the initial filament size prior to cold-working. In connection with composite filament 34, a reduction of lateral cross-sectional area in the range of about forty percent to eighty percent is preferred, and a range of about fifty-five percent to sixty-five percent is highly preferred.

The successive cold-working and annealing steps give rise to the need for matching the core and case materials, particularly as to their coefficients of thermal expansion, elastic moduli in tension, annealing temperature ranges, total elongation capacities, and also as to their crystalline structure. A good match of elastic moduli, elongation, and thermal expansion coefficients minimizes the tendency for any ruptures or discontinuities along the core/case interface as the composite filament is processed. Crystalline structures should be considered in matching core and case materials. The Elgiloy alloy, and other materials used to form case tube 32, commonly experience a transformation between the cold-work in g and aging steps, from a face centered cubic crystalline structure to a hexagonal close packed crystalline structure. The Elgiloy alloy experiences shrinkage as it undergoes this transformation. Accordingly, the core material must either experience a similar reduction, or be sufficiently ductile to accommodate reduction of the case.

There is no annealing after the final cold-working stage. At this point, composite filament 34 is formed into the shape intended for the device incorporating the filament. In FIG. 8, several filaments or strands 34a-e are helically wound about a cylindrical form 48 and held in place at their opposite ends by sets of bobbins 50a-e and 52a-e. Strands 34a-e can be individually processed, or individual segments of a single annealed and cold-worked composite filament, cut after the final cold-working stage. In either event, the filaments cooperate to form one of the two oppositely directed sets of spaced apart and parallel filaments that form a device such as stent 16. While only one set of filaments is shown, it is to be understood that a corresponding group of filaments, helically wound and intertwined about form 48 in the opposite direction, are supported by corresponding bobbins at the opposite filament ends.

A useful prosthesis depends, in part, upon correctly supporting the filaments. The filaments are maintained in tension, and it is important to select the appropriate tensile force and apply the tensile force uniformly to all filaments. Insufficient tensile force may allow wire cast or lift effects to cause the individual filaments to depart from their helical configuration when released from the bobbins, and the braided structure of the stent may unravel.

FIG. 9 illustrates two filaments 34a and 54a, one from each of the oppositely wound filament sets, supported by respective bobbins 50a/52a and 56a/58a in a furnace 60 for age hardening in a vacuum or protective atmosphere. Age hardening is accomplished at temperatures substantially lower than annealing, e.g. in the range of about 700°–1200° F., more preferably 900°–1000° F. The filaments overlie one another to form several intersections, one of which is indicated at 62. When the filaments are properly tensioned, a slight impression is formed in the overlying filament at each intersection. These impressions, or saddles, tend to positionally lock the filaments relative to one another at the intersections, maintaining the prosthesis configuration without the need for welding or other bonding of filaments at their intersections.

While only two oppositely directed filaments are illustrated as a matter of convenience, it is to be appreciated that the age hardening stage is performed after the tensioning and winding of all filaments, i.e. both oppositely directed sets. Accordingly, during age hardening, the filaments are locked relative to one another at multiple intersections. The preferred time for age hardening is about 1–5 hours. This age hardening step is critical to forming a satisfactory self-expanding prosthesis, as it substantially enhances elasticity, yield strength, and tensile strength. Typically, the elastic modulus is increased by at least 10 percent, and the yield strength (0.2% offset) and tensile strength are each increased by at least 20 percent.

Figure 10:
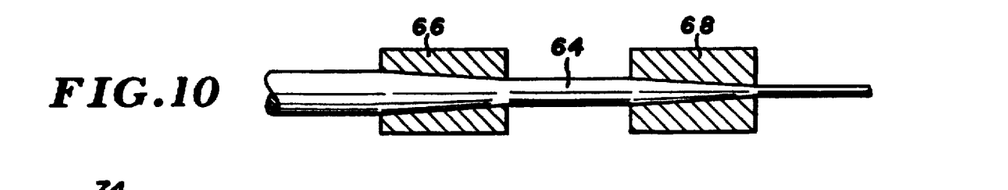
FIG. 10 schematically illustrates a swaging step of an alternative process for manufacturing the stent.

As an alternative to the process just explained, a substantially larger and shorter composite structure 64 (e.g. six inches long with a diameter of approximately two inches) can be subjected to a series of elongation and diameter reduction steps. FIG. 10 schematically illustrates two swaging dies 66 and 68, which may be used in the course of a hot working billet reduction process. Of course, any appropriate number of swaging dies may be employed. Alternatively, the diameter reduction can be accomplished by extrusion/pulltrusion at each stage. When a sufficient number of swaging steps have reduced the composite structure diameter to about 6 millimeters (0.25 inches). The composite structure or filament can be further processed by drawing it through dies and annealing, as illustrated in FIG. 6 for the previously discussed process. As before, the composite filament is ready for selective shaping and age hardening after the final cold-working stage.

Figure 5:
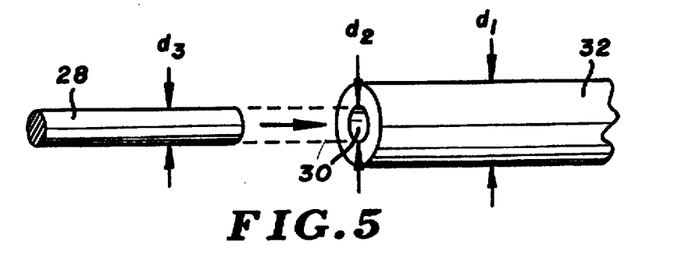
FIGS. 5–9 schematically illustrate a process for manufacturing the stent.

As compared to the process depicted in FIGS. 5–7, the swaging or pulltrusion approach involves substantially increased hot and cold-working of the composite structure or filament, and the initial assembling of the core into the case or shell tubing is easier. Given the much larger initial composite structure size, the structure is subjected to annealing temperatures for a substantially longer time, e.g. half an hour to an hour, as opposed to the one to fifteen second anneal times associated with the process depicted in FIG. 6. Consequently, particular care must be taken to avoid combinations of core and case materials with tendencies for intermetallic formation along the core/case interface. Further, the required hot working of the larger billet may not afford the same degree of metallurgical grain refinement.

Figure 11:
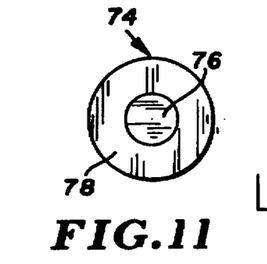
FIG. 11 is an end elevational view of an alternative embodiment filament.

FIG. 11 is an end elevation of a composite filament 74 including a central core 76 of a structural material such as the Elgiloy alloy, surrounded by a radiopaque case 78, thus reversing the respective functions of the core and case as compared to composite filament 34. Composite filament 74, as compared to filament 34, presents a larger and less refractive radiopaque profile for a given composite filament diameter. Composite filament 74, however, may be more difficult to manufacture than filaments that employ the structural material as the case.

Figure 12:
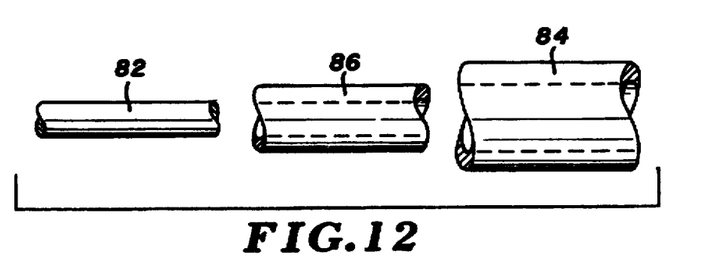
FIG. 12 is an elevational view of several components of an alternative composite filament constructed according to the present invention.
Figure 13:
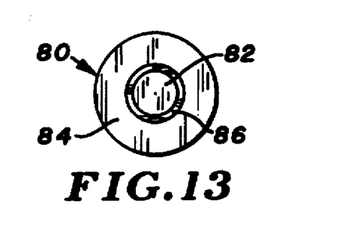
FIG. 13 is an end elevational view of the composite filament formed by the components shown in FIG. 12.

FIGS. 12 and 13 show a further alternative composite filament 80, consisting of a central radiopaque core 82, an outer annular structural case 84, and an intermediate annular layer 86 between the core and the case. Intermediate-layer 86 provides a barrier between the core and case, and is particularly useful in composite filaments employing core and case materials that would be incompatible if contiguous, e.g. due to a tendency to form intermetallics. Materials suitable for barrier layer 86 include tantalum, niobium and platinum. As suggested by FIG. 12, the core, barrier layer and case can be provided as a cylinder and two tubes, inserted into one another for manufacture of the composite filament as explained above.

Figure 14:
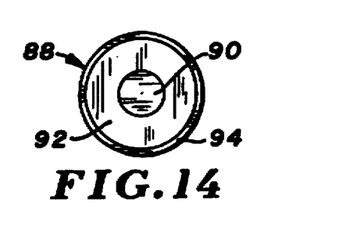
FIG. 14 is an end elevational view of another alternative embodiment composite filament.

FIG. 14 illustrates another alternative embodiment composite filament 88 having a central radiopaque core 90, a structural case 92, and a relatively thin annular outer cover layer 94. Composite filament 88 is particularly useful when the selected mechanical structure lacks satisfactory biocompatibility, hemocompatibility, or both. Suitable materials for cover layer 94 include tantalum, platinum, iridium, niobium, titanium and stainless steel. The composite filament can be manufactured as explained above, beginning with insertion of the radiopaque core into the structural case, and in turn, inserting the case into a tube formed of the cover material. Alternatively, cover layer 94 can be applied by a vacuum deposition process, as a thin layer (e.g. from ten to a few hundred microns) is all that is required.

The following examples illustrate formation of composite filaments according to the above-disclosed processes.

EXAMPLE 1

An elongate tantalum core having a diameter of 0.046 inches (1.17 mm) was assembled into an Elgiloy alloy case having an outer diameter of 0.102 inches (2.6 mm) and an inner diameter of 0.056 inches (1.42 mm). Accordingly, the lateral cross-sectional area of the tantalum core was about 25% of the composite filament lateral cross-sectional area. Composite filaments so constructed were subjected to 5–6 alternating stages of cold-working and annealing, to reduce the outer diameters of the composite filaments to values within the range of 0.004–0.0067 inches. The tantalum core diameters were reduced to values in the range of 0.002–0.0034 inches. The composite filaments were formed into a stent suitable for biliary applications, and age hardened for up to five hours, at temperatures in the range of 900°–1000° F.

EXAMPLE 2

Elongate cores of a platinum iridium alloy (20% by weight iridium), with initial core outer diameters of 0.088 inches, were inserted into annular Elgiloy cases with outer diameters of 0.098 inches and inside diameters of 0.044 inches. The resulting composite filaments were processed through about six cold-working and annealing cycles as in the first example, to reduce the outer filament diameter to values within the range of 0.00276 inches–0039 inches, and reducing the core outer diameter to values in the range of 0.0018–0.0026 inches. The core thus constituted 43% of the filament lateral cross-sectional area. The resulting filaments were formed into a small vasuclar stent, and age hardened for approximately three hours.

EXAMPLE 3

Composite filaments were constructed and processed substantially as in example 2, except that the core was formed of a platinum nickel alloy, with nickel 10% by weight.

EXAMPLE 4

The composite filaments were constructed and processed as in examples 2 and 3, except that the core was formed of tantalum, and the case was formed of MP35N alloy, and the cold-working stages reduced the filament outer diameter to values in the range of 0.00276–0.0047 inches.

In the case of all examples above, the resulting stents exhibited satisfactory elasticity and were readily fluoroscopically imaged in real time.

Each of the above described composite filaments combines the desired structural stability and resiliency, with radio-opacity that allows in vivo imaging of the device composed of the filaments, during deployment and after device fixation. This result is achieved by a drawn filled tubing process that cold works a central core and its surrounding case, to positively bond the core and case together such that the composite filament behaves as a continuous, solid structure. Performance of the filament and resulting device is further enhanced by a selective matching of the core and case materials, as to linear thermal expansion coefficient, annealing temperature, moduli of elasticity, and crystalline structure.

What is claimed is:

1. A resilient, body implantable prosthesis, including:

a plurality of elongate resilient strands, helically wound in at least two oppositely directed sets of strands arranged in a braided configuration;

wherein the strands are age-hardened and substantially uniform in lateral cross-section over respective lengths thereof, and wherein each of the strands includes an elongate core and an elongate tubular case surrounding the core at least substantially over said respective length, a lateral cross-sectional area of the core being at least about ten percent of a lateral cross-sectional area of the strand;

wherein one of the core and case is constructed of a first material having a linear attenuation coefficient of at least 25 cm$^{-1}$ at 100 KeV, the other of the core and case is constructed of a resilient second material, and the first material is more radiopaque than the second material; and wherein said strands, due at least in part to an age-hardening of the resilient second material when the strands are in said braided configuration, exhibit an enhanced modulus of elasticity which is greater than a nominal modulus of elasticity of non-age-hardened but otherwise identical strands by at least about 10 percent, and further has a greater yield strength at 0.2 percent offset and a greater tensile strength as compared to said non-age-hardened but otherwise identical strands.

2. The prosthesis of claim 1 wherein:

the first material forms the core.

3. The prosthesis of claim 2 wherein:

the first material has a direct or equivalent atomic number of at least fifty, and a density of at least 0.5 pounds per cubic inch.

4. The prosthesis of claim 3 wherein:

the first material consists essentially of at least one of the following constituents: tantalum, platinum, gold, iridium, rhenium, tungsten, ruthenium and depleted uranium.

5. The prosthesis of claim 2 wherein:

the case is substantially concentric about the core.

6. The prosthesis of claim 5 wherein:

the second material is body compatible.

7. The prosthesis of claim 6 wherein:

the second material has a yield strength (0.2 percent of offset) of at least 150,000 psi.

8. The prosthesis of claim 5 wherein:

the second material consists essentially of at least one of the following constituents: cobalt, chromium, titanium, aluminum, vanadium, chromium, nickel, molybdenum and iron.

9. The prosthesis of claim 8 wherein:

the second material consists essentially of a cobalt-based alloy.

10. The prosthesis of claim 9 wherein:

the cobalt-based alloy consists essentially of cobalt, chromium, iron, nickel, and molybdenum.

11. The prosthesis of claim 2 wherein:

a lateral cross-sectional area of the core of each strand is in the range of from ten to forty-six percent of the lateral cross-sectional area of the strand.

12. The prosthesis of claim 1 wherein:

the strands in each set are parallel to one another, and the sets of strands cooperate to form a cylinder.

13. The prosthesis of claim 1 wherein:

said second material forms the core.

14. The prosthesis of claim 1 wherein:

said strands, as compared to the non-age-hardened strands, have a yield strength at 0.2 percent offset at least about twenty percent greater, and a tensile strength at least about twenty percent greater.

15. The prosthesis of claim 1 wherein:

the resilient strands of said oppositely directed sets are spaced apart from one another.

16. The prosthesis of claim 1 wherein:

the braided configuration of the helically wound strands is radially self-expanding.

17. A body implantable prosthesis, including:

a plurality of elongate strands, helically wound in at least two oppositely directed sets of strands, arranged in a braided configuration;

wherein the strands are age-hardened and substantially uniform in lateral cross-section over respective lengths thereof, and wherein each of the strands includes an elongate core and an elongate tubular case surrounding the core at least substantially over said respective length, a lateral cross-sectional area of the core being at least about ten percent of a cross-sectional area of the core and case, combined; and wherein one of the core and case is constructed of a first material having a linear attenuation coefficient of at least 25 cm$^{-1}$ at 100 KeV, the other of the core and case is constructed of a second material having a yield strength of at least 150,000 psi at 0.2% offset, the first material is more radiopaque than the second material, and the first and second materials have about the same linear coefficients of thermal expansion; and wherein said strands, due at least in part to an age-hardening of the resilient second material when the strands are in said braided configuration, exhibit an enhanced modulus of elasticity which is greater than a nominal modulus of elasticity of non-age-hardened but otherwise identical strands by at least about 10 percent, and further has a greater yield strength at 0.2 percent offset and a greater tensile strength as compared to said non-age-hardened but otherwise identical strands.

18. The prosthesis of claim 17 wherein:

the first material forms the core.

19. The prosthesis of claim 18 wherein:

the first material has a direct or equivalent atomic number of at least fifty, and a density of at least 0.2 pounds per cubic inch.

20. The prosthesis of claim 19 wherein:

the first material consists essentially of at least one of the following constituents: tantalum, platinum, gold, iridium, rhenium, tungsten, ruthenium and depleted uranium.

21. The prosthesis of claim 17 wherein:

the second material consists essentially of a cobalt-based alloy.

22. The prosthesis of claim 21 wherein:

the cobalt-based alloy consists essentially of cobalt, chromium, iron, nickel and molybdenum.

23. The prosthesis of claim 18 wherein:

a lateral cross-sectional area of the core of each strand is in the range of from 10 to 46 percent of the lateral cross-sectional area of the core and case, combined.

24. The prosthesis of claim 17 wherein:

said second material forms the core.

25. The prosthesis of claim 17 wherein:

the first material and the second material have respective linear coefficients of thermal expansion within the range of about $3 \times 10^{-6}$ per degree F. to about $9 \times 10^{-6}$ per degree F.

26. The prosthesis of claim 17 wherein:

the strands in each of said sets are substantially parallel to one another.

27. The prosthesis of claim 17 wherein:

said strands, as compared to the non-age-hardened strands, have a yield strength at 0.2 percent offset at least about twenty percent greater, and a tensile strength at least about twenty percent greater.

28. The prosthesis of claim 17 wherein:

the elongate strands of said oppositely directed sets are spaced apart from one another.

29. The prosthesis of claim 17 wherein:

the braided configuration of the helically wound strands is radially self-expanding.

30. A resilient, body implantable prosthesis, including:

a plurality of elongate resilient strands, helically wound in at least two oppositely directed sets of strands interwoven with one another;

wherein the strands are age-hardened and substantially uniform in lateral cross-section over respective lengths thereof, and wherein each of the strands includes an elongate core and an elongate tubular case surrounding the core at least substantially over said respective length, a lateral cross-sectional area of the core being at least about ten percent of a cross-sectional area of the core and case, combined; and wherein said core is constructed of a core material having a linear attenuation coefficient of at least 25 cm$^{-1}$ at 100 KeV, the case is constructed of a resilient case material, the core material is more ductile and more radiopaque than the case material; and wherein said strands, due at least in part to an age-hardening of the case material when the strands are interwoven with one another, exhibit an enhanced modulus of elasticity which is greater than a nominal modulus of elasticity of non-age-hardened but otherwise identical strands, by at least about 10 percent.

31. The prosthesis of claim 30 wherein:

the core material has a direct or equivalent atomic number of at least fifty, and a density of at least 0.5 pounds per cubic inch.

32. The prosthesis of claim 31 wherein:

the core material consists essentially of at least one of the following constituents: tantalum, platinum, gold, iridium, rhenium, tungsten, ruthenium and depleted uranium.

33. The prosthesis of claim 30 wherein:

the case material is body compatible, and has a yield strength at 0.2 percent offset of at least 150,000 psi.

34. The prosthesis of claim 33 wherein:

the case material consists essentially of at least one of the following constituents: cobalt, chromium, titanium, aluminum, vanadium, nickel, molybdenum and iron.

35. The prosthesis of claim 33 wherein:

the case material consists essentially of a cobalt-based alloy.

36. The prosthesis of claim 35 wherein:

the cobalt-based alloy consists essentially of cobalt, chromium, iron, nickel, and molybdenum.

37. The prosthesis of claim 30 wherein:

the strands in each set are parallel to one another, and the sets of strands cooperate to form a cylinder.

38. The prosthesis of claim 30 wherein:

The core and case materials have about the same linear coefficients of thermal expansion.

39. The prosthesis of claim 30 wherein:

the strands, as compared to the non-age-hardened strands, have a yield strength at 0.2 percent offset at least about 20 percent greater, and a tensile strength at least about 20 percent greater.

40. The prosthesis of claim 30 wherein:

the resilient strands of said oppositely directed sets are spaced apart from one another.

41. The prosthesis of claim 30 wherein:

the oppositely directed sets of strands are interwoven into a self-expanding structure.

* * * * *

UNITED STATES PATENT AND TRADEMARK OFFICE
CERTIFICATE OF CORRECTION

PATENT NO. : 5,800,511

DATED : September 1, 1998

INVENTOR(S) : David W. Mayer

It is certified that error appears in the above-identified patent and that said Letters Patent is hereby corrected as shown below:

On the title page,
Under Related U.S. Application Data:

Please substitute the following:

[62] Divisional of co-pending application Serial No. 08/469,810, filed June 6, 1995, now U.S. Patent No. 5,824,077, which is a continuation of 08/006,216, filed January 19, 1993, now abandoned.

Signed and Sealed this

Twelfth Day of October, 1999

Attest:

Q. TODD DICKINSON

*Attesting Officer*  *Acting Commissioner of Patents and Trademarks*